(12) United States Patent
Prodius et al.

(10) Patent No.: US 11,090,579 B2
(45) Date of Patent: Aug. 17, 2021

(54) SEPARATING RARE EARTH METAL OXALATES

(71) Applicant: Iowa State University Research Foundation, Inc., Ames, IA (US)

(72) Inventors: Denis Prodius, Ames, IA (US); Cajetan Ikenna Nlebedim, Ames, IA (US); Anja-Verena Mudring, Stockholm (SE)

(73) Assignee: Iowa State University Research Foundation, Inc., Ames, IA (US)

( * ) Notice: Subject to any disclaimer, the term of this patent is extended or adjusted under 35 U.S.C. 154(b) by 28 days.

(21) Appl. No.: 16/350,841

(22) Filed: Jan. 22, 2019

(65) Prior Publication Data

US 2019/0160394 A1 May 30, 2019

Related U.S. Application Data

(63) Continuation-in-part of application No. PCT/US2017/000040, filed on Jul. 20, 2017.
(Continued)

(51) Int. Cl.
| | | |
|---|---|---|
| *B01D 11/04* | (2006.01) | |
| *C01F 17/10* | (2020.01) | |
| *C01F 17/20* | (2020.01) | |
| *C02F 1/54* | (2006.01) | |
| *C07C 51/48* | (2006.01) | |

(Continued)

(52) U.S. Cl.
CPC .......... *B01D 11/0492* (2013.01); *B01D 11/04* (2013.01); *C01F 17/10* (2020.01); *C01F 17/17* (2020.01); *C01F 17/20* (2020.01); *C02F 1/54* (2013.01); *C07C 51/48* (2013.01); *B01D 21/01* (2013.01); *B03D 3/00* (2013.01); *C01F 17/30* (2020.01); *C02F 2101/20* (2013.01); *C02F 2103/10* (2013.01); *C07C 55/07* (2013.01); *C22B 59/00* (2013.01)

(58) Field of Classification Search
None
See application file for complete search history.

(56) References Cited

U.S. PATENT DOCUMENTS

| | | | |
|---|---|---|---|
| 4,647,438 A | 3/1987 | Sabot | 423/21.5 |
| 5,518,703 A | 5/1996 | Dissaux | 423/592 |

(Continued)

FOREIGN PATENT DOCUMENTS

| | | |
|---|---|---|
| CN | 102676853 | 9/2012 |
| KR | 10-0174278 | 2/1999 |
| WO | WO2003/104149 | 12/2003 |

OTHER PUBLICATIONS

Ahmed et al. ("Preliminary Study for Separation of Heavy Rare Earth Concentrates from Egyptian Crude Monazite", World Academy of Science, Engineering, and Technology, 2014, 8, 866-872. (Year: 2014).*

(Continued)

*Primary Examiner* — Clare M Perrin

(57) ABSTRACT

A method is provided for separating and/or purifying different metal oxalates by mixing the different metal oxalates in an aqueous solution comprising oxalic acid and an organic base so that at least one metal oxalate is soluble and at least another metal oxalate is not soluble. Different rare earth metal oxalates and/or transition metal oxalates can be separated.

17 Claims, 2 Drawing Sheets

Related U.S. Application Data

(60) Provisional application No. 62/494,101, filed on Jul. 27, 2016.

(51) Int. Cl.
*C01F 17/17* (2020.01)
*B03D 3/00* (2006.01)
*B01D 21/01* (2006.01)
*C02F 101/20* (2006.01)
*C02F 103/10* (2006.01)
*C01F 17/30* (2020.01)
*C22B 59/00* (2006.01)
*C07C 55/07* (2006.01)

(56) References Cited

U.S. PATENT DOCUMENTS

| | | | |
|---|---|---|---|
| 5,622,679 A | 4/1997 | Yuan | 423/21.5 |
| 2009/0035202 A1 | 2/2009 | Hiraiwa | 423/263 |
| 2010/0018347 A1* | 1/2010 | Holden | C22B 3/42 75/394 |
| 2014/0311294 A1 | 10/2014 | Jacobson | 75/392 |
| 2015/0354026 A1 | 12/2015 | Kasaini | 51/418 |

OTHER PUBLICATIONS

Ahmed, Sherien et al, Preliminary Study for Separation of Heavy Rare Earth Concentrates from Egyptian Crude Monazite, World Academy of Science, Engineering, and Technology, vol. 8, No. 8, pp. 866-872, 2014.

Cote, G., Hydrometallurgy of strategic metals, Solvent Extraction and Ion Exchange, 18, (4), 703-727, 2000.

Fray, D.J., Separating Rare Earth Elements, Science, 289, (5488), pp. 2295-2296, 2000.

Jordans, A. et al., A review of beneficiation of rare earth element bearing minerals, Minerals Engineering, 41(0), 97-114, 2013.

Yan, C. et al., Rare Earth Separation in China, Tsinghua Science & Technology, 11 (2) , 241-247, 2006.

Schuler, D. et al., Final Report for the Greens/EFA Group in the European Parliament, Oko-Institut eV Darmstadt, pp. 42-49 and 105-110, 2011.

Pierre Rosso et al., Extraction and separation of rare earth elements from hydrothermal metalliferous sediments, MMinerals Engineering, Elsevier, 118, pp. 106-121, 2018.

\* cited by examiner

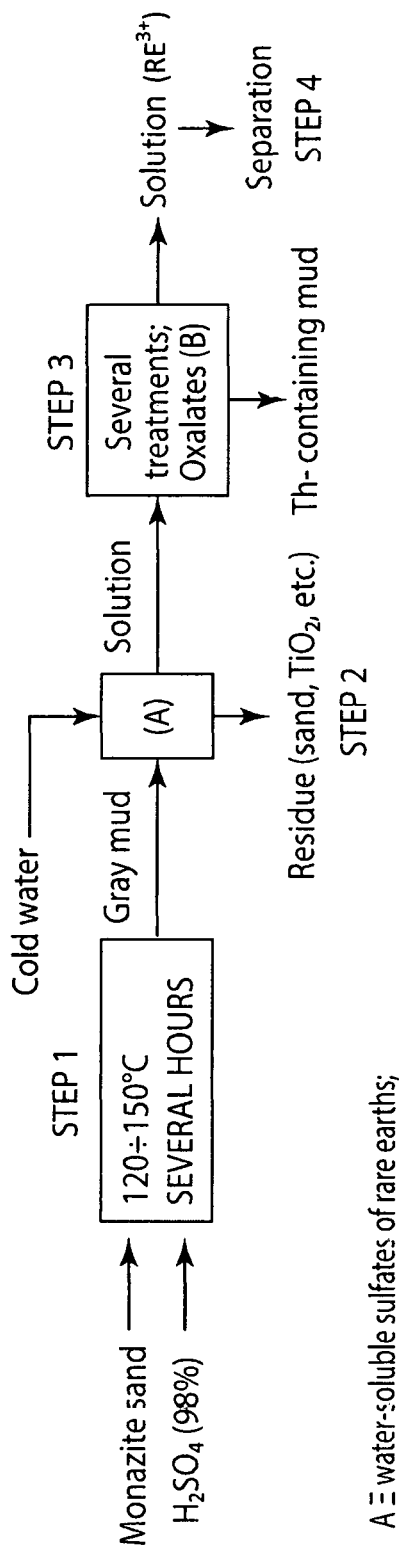

FIG. 3A

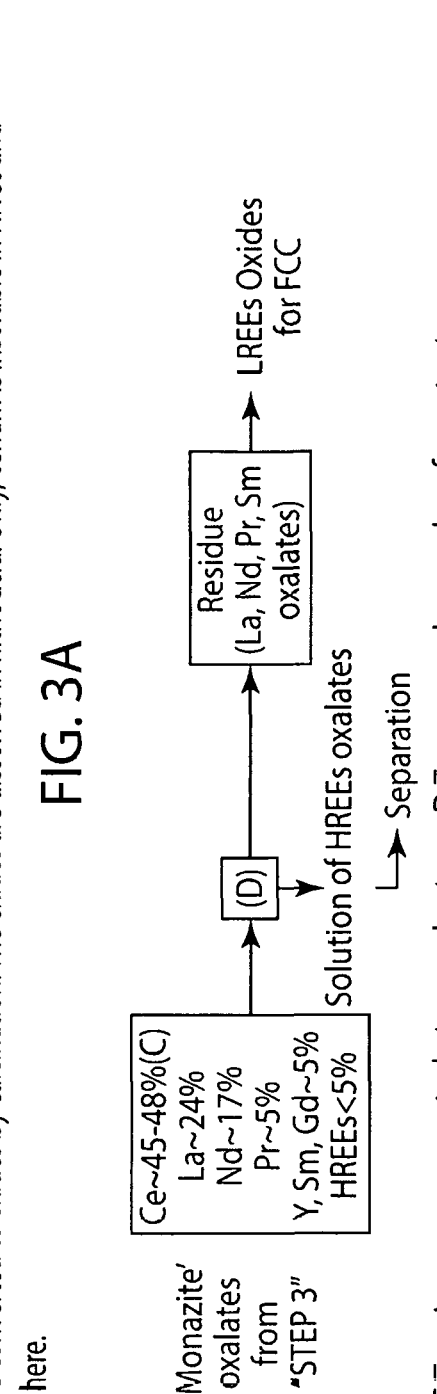

FIG. 3B

A ≡ water-soluble sulfates of rare earths;
B ≡ the acidic filtrates are partially neutralized with sodium hydroxide to pH 3-4. Thorium precipitates out of solution as the hydroxide and is removed. After that, the solution is treated with ammonium oxalate to convert rare earths to their insoluble oxalates. The oxalates are converted to oxides by calcination. The oxides are dissolved in $HNO_3$ and separated here.

C ≡ cerium was separated at an early stage; D ≡ proposed procedure for patent

SEPARATING RARE EARTH METAL OXALATES

RELATED APPLICATION

This application is a continuation-in-part application of PCT application No. PCT/US2017/000040 filed Jul. 20, 2017, which claims benefit and priority of U.S. provisional application Ser. No. 62/494,101 filed Jul. 27, 2016, the entire disclosures of which are incorporated herein by reference.

CONTRACTUAL ORIGIN OF THE INVENTION

This invention was made with government support under Grant No. DE-AC02-07CH11358 awarded by the U.S. Department of Energy. The government has certain rights in the invention.

FIELD OF THE INVENTION

The present invention relates to a method for separating/purifying rare earth metal oxalates based on solubility differences in an aqueous solution of oxalic acid and an organic base and to a rare earth metal extraction method embodying the separating/purifying step.

BACKGROUND OF THE INVENTION

The lighter rare earth elements such as lanthanum, cerium, praseodymium, and neodymium are more abundant and concentrated and usually make up about 80%-99% of a total ore deposit. The heavier elements (Gd—Lu), which are actually on average 8-125 times more expensive than the light rare earth metals (lanthanides), are less abundant but higher in demand.

Historically separation of rare earth metals can be divided into four main groups such as chemical separation, fractional crystallizations, ion-exchange methods and solvent extraction. Apart from the initial chemical separation of cerium and repeated fractional crystallization (time-consuming, up to 15000 cycles), nowadays only solvent extraction and ion-exchange methods are used on a commercial scale. Ion-exchange chromatography is not of real commercial importance for large-scale production (disadvantage is that it is a slow process) but for electronic or spectroscopic use ('phosphor grade', 99.999% purity) it is still an indispensable tool.

Solvent extraction is recognized as an important and main industrial technology for separation and purification of rare-earth elements. Acidic organophosphorus extractants, such as tributyl phosphate or di-2-ethylhexyl phosphoric acid (D2EHPA), are widely used for this purpose. Industrially the rare earths usually are recovered from the leach liquor by solvent extraction with 25% D2EHPA in kerosene, followed by multistage pulling of the rare earths from the organic solution and precipitation with oxalic acid. The final step is calcination and transformation of the rare-earth oxalates into oxides. The disadvantages of this approach are the complexity of the process and large scale use of hazardous chemicals (e.g. organophosphorus compounds). Therefore, there is an economical, ecological and strategic need in the development of new efficient low-cost extractants and extraction systems for separating them as a group or from each other.

SUMMARY OF THE INVENTION

The present invention addresses this need by providing a selective chemical separation/purification method for separating different mixed metal oxalates comprising mixing the different metal oxalates and an aqueous solution comprising oxalic acid and an organic base wherein one metal oxalate is insoluble and another metal oxalate is soluble in the aqueous solution. In certain illustrative embodiments, one metal oxalate comprises a rare earth metal oxalate and another metal oxalate comprises a different rare earth metal oxalate. In certain other illustrative embodiments, one metal oxalate comprises a rare earth metal oxalate and another metal oxalate comprises a transition metal oxalate.

A particular illustrative embodiment of the present invention provides a selective chemical separation method for a mixture of rare earth metal oxalates, wherein the method involves mixing different rare earth metal oxalates and an aqueous solution comprising oxalic acid and an organic base wherein at least one rare earth metal oxalate is soluble and at least another rare earth metal oxalate is not soluble in the aqueous solution.

In this illustrative embodiment of the invention, the different rare earth metal oxalates include at least one light rare earth metal (La—Sm) oxalate and at least one heavy rare earth (Gd—Lu) oxalate that are separated.

In still another illustrative embodiment of the invention, different heavy rare earth metal oxalates are separated.

Still another particular illustrative embodiment of the present invention provides a selective chemical purification method for a mixture of a rare earth metal oxalate contaminated with a transition metal oxalate impurity. The impure mixture and an aqueous solution comprising oxalic acid and an organic base are mixed wherein the rare earth metal oxalate is insoluble and the transition metal oxalate impurity is soluble in the aqueous solution. A purified rare earth metal oxalate containing at least 98% by weight of rare earth metal oxalate can be provided.

In other illustrative embodiments of the invention, the aqueous solution comprises 5 to 95 wt. % of oxalic acid and 95 to 5 wt. % of organic base, wherein the organic base is selected from the group consisting of organic amines, phosphines or thioesters. A preferred organic base for use in the practice of the invention comprises 1-methylimidazole.

The present invention envisions incorporating the separating and/or a purifying method of the invention as a method step in a solvent extraction method that generates rare earth metal oxalates as an intermediate reaction product. The chemical separating step of the invention is employed to separate the different rare earth metal oxalates and/or transition metal oxalates, simplifying and reducing the cost of the overall extraction process.

The practice of the present invention provides the following advantages:

1) Chemical separation of rare earth metal oxalates within two groups: La—Sm (low-priced) and Gd—Lu (high-priced).
2) Chemical separation of one or more rare earth metal oxalates from one or more transition metal oxalates present as contaminants.
3) Purification of rare earth metal oxalate mixture containing low concentrations of transition metal oxalate impurities to reduce or remove the impurities.
4) Simple and fast process because: (a) no special equipment or extreme synthetic conditions are required for the preparation of extractant; (b) it is a 'one-step' separation process which takes a few minutes.
5) Environmental Aspects: (a) It is a water-based process (no mineral acids or organic phase required); (b) The preferred organic base, 1-methylimidazole, is recognized by Sigma-Aldrich Company as a Greener Alternative Product which adheres to one or more of the "12 Principles of Green Chemistry".
6) Cost effective: The required materials (oxalic acid and the respective base), as well as the whole process, are cheaper compared to the state-of-art solvent extraction with organophosphorus compounds.
7) The separation process represents a substantial improvement to known separation technology.

The present invention will become more readily understood from the following detailed description taken with the drawings.

BRIEF DESCRIPTION OF THE DRAWINGS

FIG. 3A is a schematic diagram of a conventional solvent extraction process having four steps.

FIG. 3B is a schematic diagram of a solvent extraction process modified to include step D in accordance with an embodiment of the invention.

DESCRIPTION OF THE INVENTION

Figure 1:
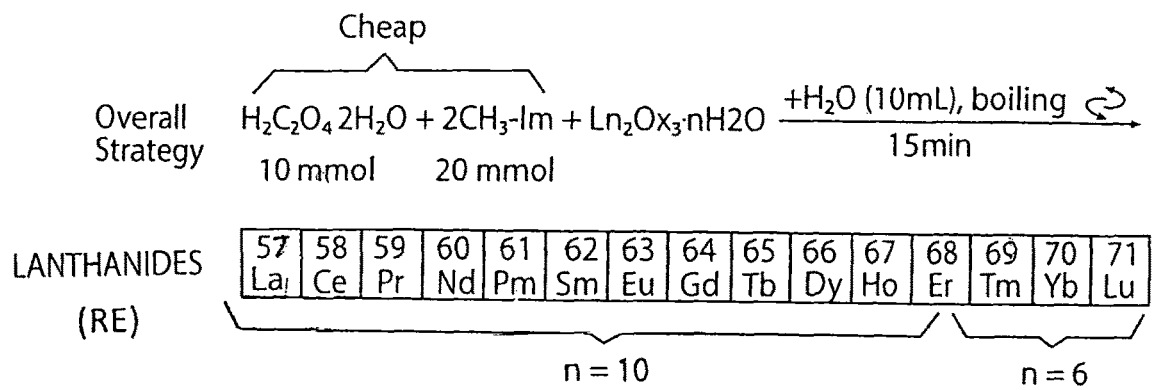
FIG. 1 is a schematic diagram of the overall chemical separation method pursuant to an illustrative embodiment of the invention.

The present invention relates to a selective chemical separation and/or purification method for separating different metal oxalates of a mixture or mass. The method involves mixing the different metal oxalates and an aqueous solution comprising oxalic acid and an organic base wherein one metal oxalate is insoluble and another metal oxalate is soluble in the aqueous solution. A certain illustrative embodiment involves treating by chemical separation/purification a mixture of a rare earth metal oxalate and another metal oxalate, which can comprise a different rare earth metal oxalate and/or a transition metal oxalate. Rare earth metals or elements include the fifteen lanthanide elements (wherein lanthanides were designated "Ln" in parent applications U.S. Ser. No. 62/494,101 and PCT/US2017/000040)), scandium, and yttrium.

Practice of certain illustrative embodiments of the invention involves mixing the different metal oxalates, which can be a main intermediate reaction product of the solvent extraction process, and an aqueous solution comprising oxalic acid and an organic base wherein one or more rare earth metal oxalates is/are soluble and one or more other metal oxalates is/are not soluble in the aqueous solution.

The aqueous solution can comprise 5 to 95 mole % oxalic acid and 95 to 5 mole % of organic base, balance being water. The aqueous solution preferably comprises 30 to 40 mole % oxalic acid and 60 mole % to 70 mole % up to 80 mole % of organic base, balance being water. The aqueous solution even more preferably comprises 32 to 34 mole % oxalic acid and 64 mole % up to 66 to 68 mole % of organic base, balance being water.

The pH of the aqueous solution typically is maintained in the range of 6 to 8, while the temperature of the aqueous solution typically is maintained between 80-100° C. in practice of the embodiments of the invention. The aqueous solution containing the rare earth metal oxalates typically is stirred or otherwise agitated during the separation method.

The organic base is selected generally from the group consisting of imidazoles, pyridines, alkylamines, benzimidazoles, histidines, phosphazene bases, or other organic bases (e.g. N-containing, P-containing, S-containing organic bases).

Particular organic bases of interest include 1-methylimidazole, 1-ethylimidazole, methylpyrrolidine, and 1-butylimidazole. A preferred organic base comprises 1-methylimidazole.

For purposes of illustration and not limitation, embodiments of the present invention can be practiced on waste material, such as for example grinding swarf, resulting from the production and/or recycling of permanent magnets, such as for example Sm—Co magnets RE-Fe—B magnets (RE is a rare earth metal or element); on waste material, such as for example scrap or waste from the manufacture and/or recycling of electrical motors and other electrical components such as terfenol-D; on untreated or treated ore; on tailings resulting from processing of ore; and on other scrap or recyclable materials containing one or more rare earth metals.

The following Examples are offered to further illustrate the practice of various embodiments of the invention without limiting the invention in any way.

Separating Rare Earth Metal Oxalates

One illustrative embodiment of the invention involves chemical separation of a mixture of one or more light rare earth metal oxalates, such as at least one of La through Sm of the Periodic Table of Elements, and one or more heavy rare earth oxalates, such as at least one of Gd through Lu of the Periodic Table of Elements.

Another illustrative embodiment of the invention involves separation of different heavy rare earth metal oxalates, such as Gd through Lu of the Periodic Table of Elements.

EXAMPLE 1

In these Examples, water-insoluble rare earth oxalates, which are one of the main intermediate products of the industrial production of rare earth metals, are selectively reacted with a mixture of oxalic acid and an organic base (e.g. mim=1-methylimidazole, eim=1-ethylimidazole, mpr=1-methylpyrrolidine), which allows for their separation based on solubility differences in the aqueous phase. FIG. 1 illustrates the overall chemical separation method pursuant to an illustrative embodiment of the invention using 1-methylimidazole (mim) as the organic base.

In a typical one stage bench-scale testing, to a solution of oxalic acid ($H_2C_2O_4.2H_2O$, 10 mmol, 1.2607 g) and the organic base (20 mmol) in 10 mL of water, a specific amount (up to about 1.6 mmol) of $RE_2Ox_3.nH_2O$ (where Ox=oxalate; n=10 (for RE=La through Er) and n=6 (for RE=Er through Lu)) was added. The mixture was stirred for 15 min at 100° C. (boiling). Each rare earth metal oxalate was added in drop-wise manner up to a maximum oxalate amount which could be dissolved in the solution (without precipitation within the 30 minutes subsequent to dropwise introduction).

A solubility distribution (SD) parameter is defined herein as the concentration of a rare earth metal in the aqueous phase. The ratio of solubility distributions (SD) between two components (concentrations of dissolved rare earth metal oxalates) is stipulated here as the separation factor ($SF_{RE}^i$) (eq. 1):

$$SF_{RE}^i = C_{RE}^i / C_{RE}^{ref} \quad (1)$$

where $C_{RE}^i$ is the concentration of a specific rare earth metal oxalate and $C_{RE}^{ref}$ is the concentration (solubility value) of the selected as a reference, low soluble, rare earth metal oxalate (e.g. Nd oxalate).

Figure 2:
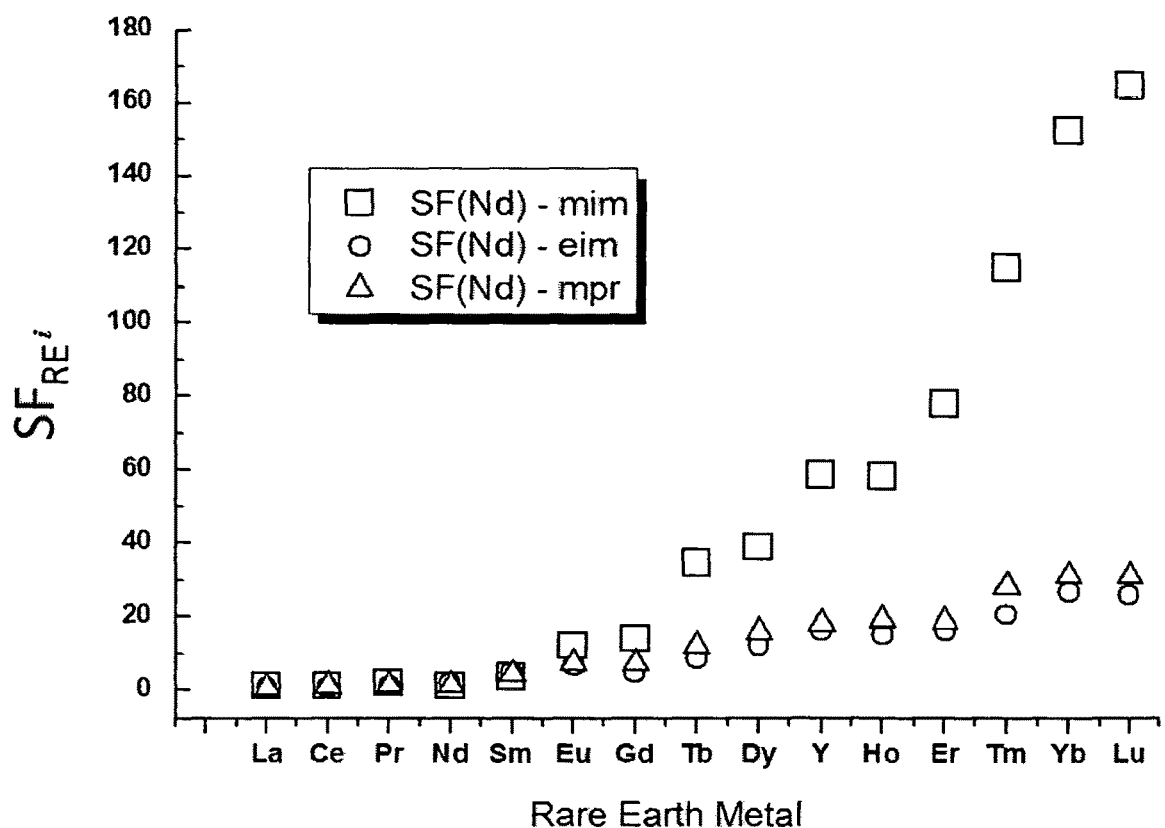
FIG. 2 is a graph of ratios of solubility distribution expressed here as separation factors, $SF_{RE}^i$, versus certain rare earth metals showing their relative solubility values in particular aqueous solutions. Each of the solution contained a different organic base/oxalic acid mixture. "SF(Nd)—base" means the separation factor of the selected rare earth metal oxalate identified as a ratio of the solubility value of that rare earth metal oxalate to the solubility value of neodymium oxalate (as a reference) in the particular aqueous solutions for the respective organic base/oxalic acid mixture.

FIG. 2 summarizes the solubility distribution (SD) values expressed as separation factor $SF_{RE}^i$ values as a function of rare earth metals tested in the manner described above. FIG. 2 reveals and demonstrates that light rare earth oxalates (LREOX, La—Sm) were practically insoluble in comparison to the heavy rare earth oxalates (HREOX, Gd—Lu) thus making it possible to transfer exclusively the HREOX to the aqueous phase.

FIG. 2 also reveals that the solubility distribution (SD) ratio values (i.e. $SF_{RE}^i$ values) as a function of the heavy rare earth oxalates (HREOX, Gd—Lu) can be used to separate different heavy rare earth metals based on solubility differences in the aqueous phase. For example, the heavy rare earth metals including at least one of Gd, Tb and Dy can be separated from at least one of Tm, Yb, and Lu based on solubility differences.

Referring to FIG. 3A, the present invention makes possible to divide different price category rare earth metals at the early stages of separation (starting already at STEP 3 instead of STEP 4 of a solvent extraction process which, as a consequence, can effectively reduce the self-cost to suppliers for rare earth (La, Ce, Pr, Nd) oxides widely used as component of FCC (Fluid Catalytic Cracking) catalyst in crude petroleum refining (see Example 2).

For example, in FIG. 3A, the starting materials are indicated to be rare earth metal-bearing monazite sand and concentrated sulfuric acid (98%). In step 1, the sand and sulfuric acid are heated at 120° C. and 150° C. for several hours. The leach liquor (gray mud) is then mixed with cold water in step 2, and the residue (e.g. sand and $TiO_2$, etc.) is allowed to settle out, leaving water-soluble sulfates of rare earth metals. This solution is afterwards partially neutralized with sodium hydroxide to pH 3-4 in step 3 to precipitate Th-containing mud (thorium hydroxide). Then, the solution is treated with ammonium oxalate to convert the rare earth metal sulfates to their insoluble oxalates. Then, in step 4, the oxalates are converted to oxides by calcination. The oxides are dissolved in nitric acid represented by "Solution ($RE^{3+}$)" to obtain the rare earth metals. Only cerium is insoluble in $HNO_3$ and separated at this stage.

EXAMPLE 2

Almost 65% of the rare earths used in the United States and Western Europe are consumed in catalysis, mainly as FCC catalysts. The application of rare earths in FCC catalysts was motivated by the need for more active and hydrothermally stable products with better yield performance. Rare earth oxides (REO) completed these goals by enhancing catalytic activity and avoiding loss of acid sites during the standard procedure. Manufacturing costs of consumer goods that contain rare earth metals may continue to decline per unit of output even as raw material costs continue to rise. Because the materials intensity (small amounts per unit output) of rare earth metals is relatively low for most end-use applications (e.g. in FCC=1-3%), low-cost manufactured goods may contain high-cost materials (heavier rare earth metals). Thus further processing, refining, and manufacturing capacity is necessary to meet growing demand and efficiencies of their uses.

The present invention provides such opportunity as shown in FIG. 3B where step D embodies a separation method pursuant to an embodiment of the invention.

In step D, the "monazite" oxalates from step 3 of the solvent extraction process of having rare earth metal amounts shown in the box (C) of FIG. 3A are treated using the aqueous solution described above in which the HREOX (heavy rare earth metal oxalates) are soluble and the LREOX (light rare earth metal oxalates) are insoluble, thus separating the heavy rare earth metals from the light rare earth metals. The residue containing light rare earth metal oxalates (e.g. La, Nd, Pr, Sm oxalates) are calcined to convert them to oxides for use as FCC catalysts.

EXAMPLE 3

Urban Mining of Dysprosium

The distinctive physical and chemical properties of rare earth elements drive their increasing demands in electronics, health care, aerospace, transportation, and defense applications. Future large-scale implementations of the above-mentioned technologies will increase the demands for neodymium and dysprosium. If efficient recycling technologies are not implemented, the demands for dysprosium and neodymium could rise by factors of 26 and 7, respectively, in the next 25 years. For example, neodymium-iron-boron magnets require a significant amount of costly dysprosium for improved high-temperature performance. However, the natural sources for dysprosium are clays currently mined only in southern China (Guangdong province). It is anticipated that recycling and recovery of precious rare earth elements from sources such as electronic waste could help to minimize the impact of any supply disruption from freshly mined materials, but the recycling rate is currently still very low (less than 1%). This is mainly due to the low concentration of these rare earth elements in such products.

A method embodiment of the invention was applied to Nd—Pr—Dy oxalates produced from the recycling of small motor Nd—Fe—B magnets (motor model RimFire no. 10 35-30-1250). In particular, in a typical one stage bench-scale testing, to a solution of oxalic acid (1.27 g) and the organic base (1-methylimidazole, 1.595 ml) in 10 mL of water, a specific amount of $RE_2(C_2O_4)_3 \cdot 10H_2O$ obtained from the recycled motor magnets (RE=Nd, Pr, Dy; 102 mg, $\%_{Dy}$=4.68% (all % by weight) was added. The mixture was stirred for 15 min at 100° C. After completing the reaction, the insoluble oxalate residue (91 mg) containing 1.49% of dysprosium (Table 1, line 8) was centrifuged, washed with water/acetone and air dried.

Also, a small amount of diluted $H_3PO_4$ (~10%) was added to the liquor solution to precipitate an RE-enriched insoluble phase ($REPO_4$). The final RE-enriched phase (~12 mg, $\%_{Dy}$=50.75) was centrifuged, washed with water/acetone and air dried.

Separation of Rare Earth Metal Oxalate and Transition Metal Oxalate

Cobalt, like the rare earth metals, has been identified as a critical material. Samarium-cobalt (Sm—Co) magnet manufacturing and processing plants can be sources of significant amounts of cobalt for secondary Co supplies. Increasing amounts of Sm—Co have been projected to be used in applications by 2020, and most of those would be available for future recycling.

EXAMPLE 4

Urban Mining of Cobalt

A method embodiment of the invention was applied to Sm—Co oxalates produced from the swarfs provided by a U.S. magnet processing company. As efficient and industrially readily available bases, 1-methylimidazole and 1-ethylimidazole were selected for individual comparative analysis alongside state-of-the-art technology (liquid-liquid extraction).

The example immediately below sets forth parameters using the 1-ethylimidazole organic organic that was preferred in this particular example. For example, in a typical one stage bench-scale testing, to a solution of oxalic acid (1.27 g) and the organic base (1-ethylimidazole, 1.970 ml) in 10 mL of water, a specific amount of $Sm_2(C_2O_4)_3 \cdot 10H_2O/CoC_2O_4 \cdot 2H_2O$ obtained directly from the recycled Sm—Co swarf (200 mg, $\%_{Co}$=72.56) (all %'s by weight) was added. The mixture was stirred for 15 min at 100° C. After completing the reaction, the insoluble residue of samarium (III) oxalate containing 0.68% of cobalt (Table 1, line 9) was centrifuged, washed twice with water (centrifuged) and air dried. From the comparative analysis (Table 1), the practice of the method embodiment of the invention proved to be operationally simple and at least 100 times faster.

The aqueous Co(II)-containing solution comprising complex organic cation/cobalt oxalate can be treated by extracting agents for further recovering of Co.

Purification of Rare Earth Metal Oxalates

An initial first separation step was practiced using a modified method embodiment described in US2018/0312941A1 (inventors: Mudring, Prodius, Nlebedim and disclosure of which is incorporated herein by reference) to produce starting "contaminated" mixtures for subsequent purification as described below in Examples 5 and 6. The first separation step involved particular modified parameters and compositions; namely: a) starting materials were mixtures of rare earth metal oxalates and transition metal (TM) oxalates taken from the recycling of respective magnet swarfs; b) the minimum reaction time was changed from 15 to 30 minutes; and c) for improved results, the mixture of oxalates was added slowly to the aqueous solution of extractant (solution containing oxalic acid and the organic base).

The first modified separation step produced an initial purity of rare earth metal content of about 92 weight % (Nd—Pr) that was the starting "contaminated" oxalate material for Example 5 and of about 97.4 weight % Sm that was the starting "contaminated" oxalate material for Example 6 where the contaminants were transition metal oxalates.

The detailed examples set forth below involve selective chemical purification method embodiments applied to these "contaminated" mixtures to produce a purified rare earth metal oxalate containing at least 98 weight % of rare earth metal oxalate.

EXAMPLE 5

Second Step (Removal of Low Concentrated Impurities (TM, ≤8.0 weight %) from Nd—Pr Oxalates)

In particular, in a typical one stage bench-scale testing, to a solution of oxalic acid (1.27 g) and the organic base (1-methylimidazole, 1.595 ml) in 10 mL of water, a specific amount equal to 1.0 g of $RE_2(C_2O_4)_3 \cdot 10H_2O/TM(C_2O_4)_n$ mixture (RE=Nd, Pr, Dy; $\%_{RE}$=92.04 (all %'s by weight); TM=transition metal impurities including one or more of Fe, Co, Ni, Cu, Zr, Zn and others) obtained from the recycled (decrepitated) hard disk drive (HDD) magnets was added. The mixture was stirred for 30 min at 100° C. After completing the reaction, the insoluble oxalate residue containing >98% of rare earth metals (Table 1, line 10), which residue was centrifuged, washed with water/acetone and air dried.

Amounts of transition metals impurities extracted from the RE/TM oxalates mixture were (confirmed by XRF analysis): Fe, >70%; Co, >80%; Ni, >97%; Cu, >77%; Zn, >81%, all %'s by weight.

Final RE content purity: >98%

These purifying embodiments of the present invention can be practiced with respect to recovery of light rare earth metal oxalates that are recovered from ore/tailings/electronic waste. These recovered light rare earth metal oxalates can have a number of impurities (especially transition metals) which may require additional purification steps. Using existing processes to purify such material with low level of contaminations would be expensive and also require disparate amounts of hazardous chemicals (organic solvents, acids, P-containing ligands, etc.) However, using the purifying embodiments of the present invention (low-cost, non-phosphorus, non-acidic and efficient) can be less expensive and safer than in other existing recovery processes.

EXAMPLE 6

Removal of Low Concentrated Impurities (TM, ≤2.5 Weight %) from Sm/RE Oxalates In a typical one stage bench-scale testing, to a solution of oxalic acid (1.27 g) and the organic base (1-methylimidazole, 1.595 ml) in 10 mL of water, a specific amount equal to 2.4 g of $RE_2(C_2O_4)_3 \cdot 10H_2O/TM(C_2O_4)_n$ mixture (RE=Sm, Nd; TM=transition metal impurities including one or more of Fe, Co, Ni, Cu, Zr, Zn and others) obtained from the recycled Sm—Co swarf ($\%_{RE}$=97.38) (all %'s by weight) was added. The mixture was stirred for 30 min at 100° C. After completing the reaction, the insoluble oxalate residue contained >99% of rare earth metals (Table 1, line 11), which residue was centrifuged, washed with water/acetone and air dried.

Amounts of low-concentrated transition metals impurities extracted from the RE/TM oxalates mixture were (confirmed by XRF analysis): Fe, >62%; Ni, >87%; Zn, >33%; Zr, >62% (all %'s by weight). Final RE content purity: >99%.

The recovery process steps set forth above can be employed with respect to Sm—Co magnets that excel the high-performance Nd—Fe—B magnets when high-temperature applications are required and possess better corrosion resistance. As mentioned in Example 2, the growing need in samarium-cobalt magnets (including airspace and military applications) have been estimated by 2020. The global prices of high purity samarium are relatively very low (e.g. ~5USD per kg of samarium oxide, >99 weight % purity) mainly as result of almost monopoly rare earth metal market. For that reason, the recycling and purification of samarium magnets will be, most certainly, not profitable. Application of low-cost recycling/purifying embodiments of the invention can diversify the supply chain of samarium feedstock.

TABLE 1

Comparative analysis of exemplary embodiments of the invention (designated CSEREOX) and existing liquid-liquid extraction method (LLE). All %'s are by weight.

| line | Parameter | Procedure | |
|---|---|---|---|
| | | CSEREOX | D2EHPA-LLE |
| 1 | Ligands | Commercial | Commercial |
| 2 | Phosphorous-ligands | No | Yes |
| 3 | Critical metal source | Oxalates | chlorides, nitrates |
| 4 | Solvents | only water | kerosene, hexane, water |
| 5 | Use of acid | No | Yes |
| 6 | Minimum number of separation cycles | 1 | >25 |
| 7 | SF (Nd vs Dy) | 38 | 41.5 |

| | Critical Metal Concentration | Before extraction (%) | After extraction (%) | Efficiency | — |
|---|---|---|---|---|---|
| 8 | Proof-of-concept #3 (Nd/Pr vs Dy) | 4.68 | 1.49 | >68% (Dy) | Industrially applied (LLE) |
| 9 | Proof-of-concept #4 (Sm vs Co) | 72.56 | 0.68 | >99% (Co) | Industrially applied (LLE) |
| 10 | Proof-of-concept #5 (Nd/Pr vs TM impurities) | 92.04 | >98.0 | >98% (Nd-Pr) | Industrially applied (LLE) |
| 11 | Proof-of-concept #6 (RE vs TM impurities) | 97.38 | >99.0 | >98% (Sm, Nd) | Industrially applied (LLE) |
| 12 | Reaction time | 15 min (for #3 and #4) and 30 min (#5 and #6) | | | >1-3 days |

SF is separation factor as it was specified above (Example 1, Eq. 1).

The present invention is advantageous in that chemical separation of rare earth oxalates within two groups: La—Sm (low-priced) and Gd—Lu (high-priced) is achievable in a 'one step' separation process, which takes a few minutes as compared to hours. The present invention is further advantageous in that selective chemical purification of impure oxalate material can be achieved to produce a purified rare earth metal oxalate containing at least 98% weight % rare earth metal oxalate.

Method embodiments of the invention are cost-effective since the required materials (oxalic acid and the respective organic base), as well as the whole process, are cheaper compared to the state-of-art solvent extraction with organophosphorus compounds. Moreover, method embodiments are simple and fast and need no special equipment or extreme synthetic conditions for the extractant preparation.

While the invention has been described in terms of specific embodiments thereof, it is not intended to be limited thereto but rather only to the extent set forth in the following claims.

We claim:

1. A method of separating at least one light rare earth metal oxalate that includes at least one of La through Sm of the Periodic Table from at least one other metal oxalate comprising at least one of a transition metal oxalate and a heavy rare earth metal oxalate that includes at least one of Gd though Lu of the Periodic Table without using mineral acid, wherein the method comprises providing the at least one light rare earth metal oxalate and the at least one other metal oxalate in an aqueous solution comprising oxalic acid and an organic base that is selected from the group consisting of N-containing organic base, P-containing organic base, and S-containing organic base and having a pH of 6 to 8 without inorganic base present to form an aqueous separation solution in which the at least one light rare earth metal oxalate is insoluble and selectively separates out of the aqueous separation solution as an insoluble residue and the at least one other metal oxalate is soluble and remains in the aqueous separation solution, thereby separating the at least one light rare earth metal oxalate from the at least one other metal oxalate in the aqueous separation solution without use of mineral acid.

2. The method of claim 1 wherein the at least one other metal oxalate includes different heavy rare earth metal oxalates wherein the heavy rare earth oxalates include at least two of Gd through Lu of the Periodic Table of Elements.

3. The method of claim 2 wherein the different heavy rare earth metal oxalates include at least one of Gd, Tb, and Dy and at least one of Tm, Yb, and Lu.

4. The method of claim 1 wherein said at least one other metal oxalate comprises a transition metal oxalate.

5. The method of claim 4 wherein the transition metal oxalate comprises at least one of cobalt oxalate, nickel oxalate, iron oxalate, copper oxalate, zirconium oxalate, and zinc oxalate.

6. The method of claim 1 wherein the said at least one light rare earth metal oxalate comprises Sm oxalate and the said at least one other metal oxalate comprises Co oxalate.

7. The method of claim 1 wherein the oxalic acid comprises 30 to 40 mole % and the organic base comprises 60 to 70 mole % of the aqueous solution.

8. The method of claim 1 wherein the organic base comprises 1-methylimidazole.

9. A method of purifying an impure oxalate mixture, comprising providing at least one rare earth metal oxalate and at least one transition metal oxalate impurity and in a mineral acid-free aqueous solution comprising oxalic acid and an organic base that is selected from the group consisting of N-containing organic base, P-containing organic base, and S-containing organic base and having a pH of 6 to 8 without inorganic base present to form an aqueous separation solution in which the at least one rare earth metal oxalate is insoluble and selectively separates out of the aqueous separation solution as an insoluble residue and the at least one transition metal oxalate impurity is soluble in the aqueous separation solution and remains in the aqueous separation solution, wherein the insoluble residue as dried consists essentially of at least 98% purity by weight of said at least one rare earth metal oxalate, thereby separating the at least one rare earth metal oxalate and the transition metal oxalate impurity in the aqueous separation solution without use of mineral acid.

10. The method of claim 9 wherein the at least one rare earth metal oxalate comprises an oxalate including at least one of La, Ce, Pr, Nd, Pr, Sm, Eu, Gd, Tb, Dy, Ho, Er, Tm, Yb, Lu, Sc, and Y.

11. The method of claim 9 wherein the at least one transition metal oxalate impurity comprises at least one of cobalt oxalate, nickel oxalate, iron oxalate, copper oxalate, zirconium oxalate, and zinc oxalate.

12. The method of claim 9 wherein the at least one transition metal impurity comprises 8 weight % or less of the impure mixture.

13. The method of claim 9 wherein the impure oxalate mixture is obtained from at least one of waste material from production of permanent magnets, waste material from the production of electrical components, ore containing a rare earth metal and a transition metal, and ore tailings containing a rare earth metal and a transition metal.

14. In a solvent extraction method of rare earth metals wherein rare earth metal oxalates are preformed as a mixture comprising at least one light rare earth metal oxalate that includes at least one of La through Sm of the Periodic Table and at least one other metal oxalate that comprises at least one of a transition metal oxalate and a heavy rare earth metal oxalate that includes Gd through Lu of the Periodic Table the subsequent step of separating the at least one light rare earth metal oxalate from the mixture by a mineral acid-free one-step separation process comprising mixing the mixture and an aqueous solution of oxalic acid and organic base that is selected from the group consisting of N-containing organic base, P-containing organic base, and S-containing organic base and having a pH of 6 to 8 without inorganic base present to form an aqueous separation solution in which the at least one light rare earth metal oxalate is insoluble and selectively separates out of the aqueous separation solution as an insoluble residue and the at least one other metal oxalate is soluble and remains in the aqueous separation solution, thereby separating the at least one light rare earth metal oxalate from the at least one other metal oxalate in the aqueous separation solution without use of mineral acid.

15. The method of claim 14 wherein the heavy rare earth metal oxalate includes at least two of Gd through Lu of the Periodic Table of Elements.

16. The method of claim 15 wherein the heavy rare earth metal oxalate includes at least one of Gd, Tb, and Dy and at least one of Tm, Yb, and Lu.

17. The method of claim 14 wherein the oxalic acid comprises 30 to 40 mole % and the organic base comprises 60 to 70 mole % of the aqueous solution.

* * * * *